United States Patent
Reilman et al.

(10) Patent No.: US 7,550,621 B2
(45) Date of Patent: Jun. 23, 2009

(54) PROCESS OF SULFATING SELECT POLYMERS

(75) Inventors: Randall Thomas Reilman, Cincinnati, OH (US); Jeffrey John Scheibel, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 155 days.

(21) Appl. No.: 11/083,810

(22) Filed: Mar. 18, 2005

(65) Prior Publication Data

US 2005/0209476 A1    Sep. 22, 2005

Related U.S. Application Data

(60) Provisional application No. 60/554,576, filed on Mar. 19, 2004.

(51) Int. Cl.
*C07C 305/00* (2006.01)
(52) U.S. Cl. ........................................................ 558/20
(58) Field of Classification Search .................. 558/20
See application file for complete search history.

(56) References Cited

U.S. PATENT DOCUMENTS

| | | | |
|---|---|---|---|
| 6,452,035 B2 | 9/2002 | Dupont et al. | |
| 7,163,985 B2 * | 1/2007 | Ortiz et al. | 525/404 |

FOREIGN PATENT DOCUMENTS

| | | |
|---|---|---|
| DE | 705 357 C | 4/1941 |
| GB | 935 649 A | 9/1963 |
| GB | 935 650 A | 9/1963 |
| GB | 1 087 415 A | 10/1967 |
| WO | WO 01/05874 A1 | 1/2001 |
| WO | WO 01/29112 A1 | 4/2001 |
| WO | WO 02/12179 A | 2/2002 |
| WO | WO 2004/020563 A | 3/2004 |
| WO | WO 2004/024858 A | 3/2004 |

* cited by examiner

*Primary Examiner*—Rei-tsang Shiao
(74) *Attorney, Agent, or Firm*—Stephen T. Murphy; Laura R. Grunzinger

(57) ABSTRACT

A process for sulfating alkoxylated amines, alkoxylated polyols, hydrophobic polyamine ethoxylate polymers, via the use of sulfuric acid.

12 Claims, No Drawings

PROCESS OF SULFATING SELECT POLYMERS

CROSS REFERENCE TO RELATED APPLICATION

This application claims priority under 35 U.S.C. § 119(e) to U.S. provisional application No. 60/554,576, filed Mar. 19, 2004.

FIELD OF THE INVENTION

The present invention relates to a process for sulfating select oligomers and polymers via the use of sulfuric acid.

BACKGROUND OF THE INVENTION

Processes for sulfation often utilized in laboratories include the use of chlorosulfonic acid, which are then not feasible industrially as hydrochloric gas evolution and corrosion issues do not allow for use of chlorosulfonic acid without, for example, costly, corrosion resistant equipment. Current commercial sulfation routes, such as falling film sulfur trioxide, give exhaustively high levels of sulfation and do not tolerate much water in the reaction mixtures. Therefore, there exists a need to have a commercially viable route for sulfation of alkoxylated amines, quaternized, alkoxylated amines, alkoxylated polyols, poly(alklene glycols), and mixtures thereof giving a controlled level of sulfation that can also tolerate the presence of water in the starting oligomer/polymer materials.

SUMMARY OF THE INVENTION

The present application relates to a process for sulfating oligomers and polymers comprising the steps of:

a) sulfating an oligomer or polymer selected from the group consisting of alkoxylated amines, alkoxylated polyols, hydrophobic polyamine ethoxylate polymers, and any mixture thereof; by the addition of sulfuric acid to make a sulfated oligomer and water mixture;

b) optionally driving off the water from the sulfated oligomer or polymer and water mixture to make a dried sulfated oligomer or polymer mixture;

c) neutralizing the sulfated oligomer or polymer mixture of step (a) or optionally the dried sulfated oligomer or polymer mixture of step (b) by mixing with neutralization agent.

The present application further relates to a process wherein sulfuric acid is added to a oligomer or polymer selected from the group consisting of alkoxylated amines, alkoxylated polyols, hydrophobic polyamine ethoxylate polymers, and any mixture thereof; in a molar amount according to formula (I):

Mole amount of oligomer/polymer*# site available for sulfation*desired % level of sulfation for # sites available for sulfation.

The present invention further relates to a method of determining the molar amount of sulfuric acid for sulfation of an oligomer or polymer selected from the group consisting of alkoxylated amines, alkoxylated polyols, hydrophobic polyamine ethoxylate polymers, and any mixture thereof; via the use of formula (I):

Mole amount of oligomer/polymer*# site available for sulfation*desired % level of sulfation for # sites available for sulfation.

DETAILED DESCRIPTION OF THE INVENTION

Incorporated and included herein, as if expressly written herein, are all ranges of numbers when written in a "from X to Y" format. It should be understood that every limit given throughout this specification will include every lower, or higher limit, as the case may be, as if such lower or higher limit was expressly written herein. Every range given throughout this specification will include every narrower range that falls within such broader range, as if such narrower ranges were all expressly written herein.

The process of this application is for controlled sulfation of oligomers/polymers selected from the group comprising alkoxylated amines, alkoxylated polyols, hydrophobic polyamine ethoxylate polymers, and any mixture thereof; through the use of sulfuric acid directly as a sulfating agent or a combination of sulfuric acid, dimethyl sulfate and water or alcohol at an acidic pH via a trans sulfation route as the sulfating agents.

The process of this application gives a controlled sulfation process for the defined classes of oligomer/polymers, where as used herein "controlled sulfation" means that a desired level of sulfation from 0.1% of available sulfation sites, to 100% of available sulfation sites are sulfated to attain a predetermined amount of sulfation of the defined classes of oligomer/polymer.

The predetermined amount of sulfation is determined according to the following formula (1):

Mole amount of oligomer/polymer*# site available for sulfation*desired % level of sulfation for # sites available for sulfation      Formula (I)

For example, if the following oligomer/polymer of formula (II)

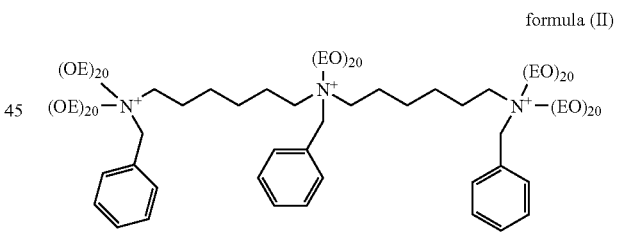

formula (II)

were to be sulfated to a level of 25% of the sites available for sulfation, formula (I) can be determined as follows:

mole of formula (II)*5 (sites available for sulfation)*0.25 (for 25% conversion of —OH to sulfate). Assuming 100% conversion of sulfuric acid. EO represents ethoxy moieties terminating in a —OH moiety and represent sites available for sulfation.

Oligomer/Polymer Classes

As will be apparent to those skilled in the art, an oligomer is a molecule consisting of only a few monomer units while polymers comprise considerably more monomer units. For the present invention, oligomers are defined as molecules having a weight average molecular weight below about 1,000 daltons and polymers are molecules having a weight average molecular weight of greater than about 1,000 daltons.

Suitable oligomers and polymer classes for use in the process of this application include oligomers/polymers selected from the group comprising alkoxylated amines, alkoxylated polyols, hydrophobic polyamine ethoxylate polymers, and any mixture thereof. As used hereinafter "oligomer" is intended to mean either oligomers or polymers of the suitable classes for use in the process of this application.

Alkoxylated Amines

Suitable alkoxylated amines for use in the process of the present application include those discussed in EP 111965 B; U.S. Pat. No. 4,548,744; WO 97/00936; and WO 99/97352. Diamines and polyamines are included in the general discussion of these references.

A preferred alkoxylated polyamine oligomer or polymer as a starting material for the present process is a polyamine having the formula (III):

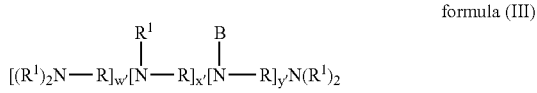

formula (III)

wherein each R unit of formula (III) is selected from formula (IV)

$$—(R^3O)_wR^4—$$ formula (IV)

wherein $R^3$ and $R^4$ of formula (IV) are each independently selected from the group consisting of $C_2$-$C_8$ linear alkylene, $C_3$-$C_8$ branched alkylene, phenylene, substituted phenylene, and mixtures thereof; the index w of formula (IV) is from 0 to 10, and can be from about 2 to about 10. As used herein, "branched" is intended to mean a $C_1$-$C_{15}$ alkyl branch on the indicated moiety, preferably a $C_1$-$C_4$ alkyl branch.

$R^1$ units of formula (III) are formula (IV):

$$—(R^2O)_tY$$ formula (IV)

wherein $R^2$ of formula (IV) is ethylene, 1,2-propylene, and mixtures thereof; Y of formula (IV) is hydrogen, and the value of the index t of formula (IV) is from 1 to 100. Preferably the values of the indices w', x', and y' of formula (III) are such that the polyamine has a backbone weight average molecular weight prior to modification of from 600 daltons to about 3000 daltons. Preferred backbone weight average molecular weights are 600 daltons, 1200 daltons, 1800 daltons, and 3000 daltons.

An example of a preferred alkoxylated polyamine polymer as a starting material of the present process is a polyamine wherein each R of formula (III) is ethylene and the backbone has a weight average molecular weight of about 3000 daltons and each hydrogen of the backbone amino units are substituted by formula (IV) wherein either one or three 1,2-propyleneoxy units are directly attached to the polyamine chain followed by sufficient ethyleneoxy units to provide formula (IV) which has an average of 10 to 30 alkyleneoxy units present (i.e., t of formula (IV) averages from 10 to 30).

Preferred alkoxylated polyamine oligomers or polymers as starting materials for the present process is a polyamine having the formula (V):

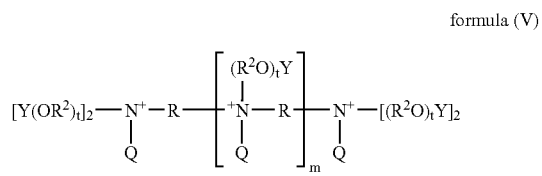

formula (V)

wherein R of formula (V) have the formula $—(R^3O)_wR^4—$ wherein $R^3$ and $R^4$ are each independently selected from the group consisting of $C_2$-$C_8$ linear alkylene, $C_3$-$C_8$ branched alkylene, phenylene, substituted phenylene, and mixtures thereof. As used herein, "branched" is intended to mean a $C_1$-$C_{15}$ alkyl branch on the indicated moiety, preferably a $C_1$-$C_4$ alkyl branch. $R^2$ of formula (V) is ethylene, 1,2-propylene, and mixtures thereof; Y of formula (IV) is hydrogen, and the value of the index t of formula (IV) is from 1 to 100, preferably from 15 to 25. The index m is from 0 to 20, preferably from 0 to 10, more preferably from 0 to 4, yet more preferably from 0 to 3, most preferably from 0 to 2. The index w is from 1 to 10, preferably from about 2 to about 10.

Suitable starting materials for the process of the present invention include formula (II) and formula (VI):

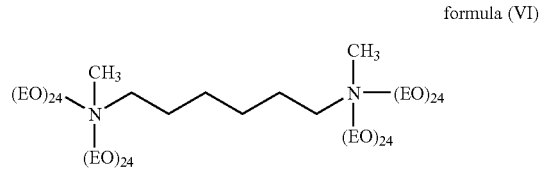

formula (VI)

wherein EO of formula (VI) represent ethoxy moieties termination in an —OH moiety.

Alkoxylated Polyols

Another oligomer or polymer suitable for use as a starting material in the present process includes polyol compounds comprising at least three hydroxy moieties, preferably more than three hydroxy moieties. Most preferably six or more hydroxy moieties. At least one of the hydroxy moieties further comprising a alkoxy moiety, the alkoxy moiety is selected from the group consisting of ethoxy (EO), propoxy (PO), butoxy (BO) and mixtures thereof preferably ethoxy and propoxy moieties, more preferably ethoxy moieties. The average degree of alkoxylation is from about 1 to about 100, preferably from about 4 to about 60, more preferably from about 10 to about 40. Alkoxylation is preferably block alkoxylation.

Suitable polyol compounds for starting materials for use in the present invention include maltitol, sucrose, xylitol, glycerol, pentaerythitol, glucose, maltose, matotriose, maltodextrin, maltopentose, maltohexose, isomaltulose, sorbitol, poly vinyl alcohol, partially hydrolyzed polyvinylacetate, xylan reduced maltotriose, reduced maltodextrins, polyethylene glycol, polypropylene glycol, polyglycerol, diglycerol ether, polymers grafted with alkylene oxide, including but not limited to acrylates and polyacrylates grafted with alkylene oxide, other suitable polymers containing alkylene oxide substituents and mixtures thereof. Preferably the polyol compound is selected from sorbitol, maltitol, sucrose, xylan, polyethylene glycol, polypropylene glycol and mixtures thereof. Preferably the polyol compound is selected from sorbitol, maltitol, sucrose, xylan, and mixtures thereof.

Tuning of the polyol compounds can be derived via one or more modifications, dependant upon the desired formulability and performance requirements. Tuning can include incorporating an anionic, cationic, or zwitterionic charge modifications to the polyol compounds.

In one embodiment of the present invention, at least one hydroxy moiety comprises an alkoxy moiety.

Hydrophobic Polyamine Ethoxylate Polymers

Materials suitable for use as starting materials in the process of the present application include hydrophobic polyamine ethoxylate polymers characterized by comprising a general formula (VII):

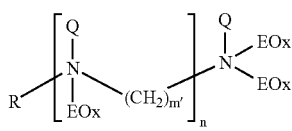

formula (VII)

R of formula (VII) is a linear or branched $C_1$-$C_{22}$ alkyl, a linear or branched $C_1$-$C_{22}$ alkoxyl, linear or branched $C_1$-$C_{22}$ acyl, and mixtures thereof; preferably R of formula (VII) is a linear $C_{12}$ to $C_{18}$ alkyl. As used herein, "branched" is intended to mean a $C_1$-$C_{15}$ alkyl branch on the indicated moiety, preferably a $C_1$-$C_4$ alkyl branch. The alkyl, alkoxyl, and acyl may be saturated or unsaturated, preferably saturated. The n index of formula (VII) is from about 2 to about 9, preferably from about 2 to about 5, most preferably 3. Wherein EO of formula (VII) represent ethoxy moieties termination in an —OH moiety.

Q of formula (VII) is independently selected from an electron pair, hydrogen, methyl, ethyl, and mixtures thereof. If the formulator desires a neutral backbone of the hydrophobic polyamine ethoxylate, Q of formula (VII) should be selected to be an electron pair or a hydrogen. Should the formulator desire a quaternized backbone of the hydrophobic polyamine ethoxylate, at least on Q of formula (VII) should be chosen from methyl, ethyl, preferably methyl. The m index of formula (VII) is from 2 to 6, preferably 3. The index x of formula (VII) is independently selected to average from about 1 to about 70 ethoxy units, preferably an average from about 20 to about 70, preferably about 30 to about 50, for polymers containing nonquaternized nitrogens; preferably from about 1 to about 10 for polymers containing quaternized nitrogens.

In another embodiment of the present invention, the nitrogens of the hydrophobic polyamine ethoxylate are given a positive charge through quaternization. As used herein "quaternization" means quaternization or protonization of the nitrogen to give a positive charge to the nitrogens of the hydrophobic polyamine ethoxylate.

The tuning or modification may be combined depending upon the desired formulability and performance requirements. Specific, non-limiting examples of preferred hydrophobic polyamine ethoxylate of the present invention include structure 22 above and formula (VIII):

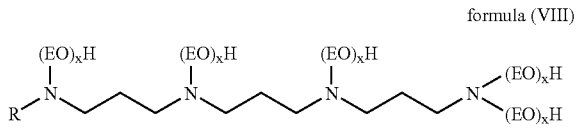

formula (VIII)

wherein R of formula (VIII) is a linear or branched $C_{12}$-$C_{16}$ alkyl, and mixtures thereof; x of formula (VIII) is from about 20 to about 70. Wherein EO of formula (VIII) represent ethoxy moieties.

Process

The process of the application comprises the steps of:

a) sulfating an oligomer selected from the group comprising alkoxylated amines, alkoxylated polyols, hydrophobic polyamine ethoxylate polymers, and any mixture thereof; by the addition of sulfuric acid to make a sulfated oligomer and water mixture;

b) optionally driving off the water from the sulfated oligomer and water mixture to make a dried sulfated oligomer;

c) neutralizing the sulfated oligomer or polymer mixture of step (a) or optionally the dried sulfated oligomer or polymer mixture of step (b) by mixing with a neutralization agent.

Step (a) Sulfation Step

The sulfation step of the application comprises adding sulfuric acid in a predetermined amount to an oligomer (again as stated above "oligomer" is intended to mean both oligomers and polymers) selected from the group comprising alkoxylated amines, alkoxylated polyols, hydrophobic polyamine ethoxylate polymers, and any mixture thereof; to attain the desired level of sulfation for the oligomer. The amount of sulfuric acid is predetermined by formula (I):

Mole amount of oligomer*# site available for sulfation*desired % level of sulfation for # sites available for sulfation          Formula (I)

to form a sulfated oligomer and water mixture. The oligomer will be in its acid form at the end of step (a). Excess sulfuric acid may be utilized as determined by formula (I).

Water, in limited amounts, may optionally be present in step (a) with the oligomer before the sulfation step is completed. This is discussed more below.

In addition to the sulfuric acid, dimethyl sulfate may also be used in combination with a strong acid, preferably a non-sulfating acid such as methanesulfonic acid, and water as the sulfating agent. The mixture of water to oligomer when the step utilizes sulfuric acid and dimethyl sulfate (with a strong acid) is in a ratio of 0:1 (anhydrous) to 0.99 to 0.01. If dimethyl sulfate is utilized, then step b) below will also include driving off any resulting methanol generated during the sulfation step from the sulfated oligomer and water mixture.

Optional Step (b) Driving Step

The optional driving step to remove water, and potentially methanol, from the sulfated oligomer and water mixture can be done at various temperatures and pressures, dependent upon the desire for speed and color purity of the resulting dried sulfated oligomer of the process. Color of the resulting dried sulfated oligomer may be impacted by the use of too high of a temperature; therefore, the use of a reduced pressure (vacuum) to drive off water is step that may be utilized in the present process. Alternatively, removal of water can be accomplished by the use of an inert solvent that azeotropes with water, such as benzene, to facilitate the water removal. Alternatively, water may be removed by sparging the sulfated oligomer and water mixture with inert gas. Suitable inert gases, such as nitrogen, are known by one of skill in the art.

The amount of water that is acceptable remaining after step (b) as part of the dried sulfated oligomer is from 0.01 wt % to 20 wt % by weight of the dried sulfated oligomer.

Acceptable temperature ranges are such that if the sulfated oligomer of the sulfated oligomer and water mixture is a solid, that the sulfated oligomer is fluid enough to mix. Higher temperatures increase the rate of removal of the water from the sulfated oligomer and water mixture, but, without being bound by a theory, is believed not to play a significant role in the actual sulfation. Higher temperatures do, however, increase the rate of reaction, but also may reduce the color purity of the dried sulfated oligomer and may increase the amount of undesired side reactions. Temperatures can range from 20° C. to 150° C. If the oligomer comprises a quaternized nitrogen, temperatures may range from 20° C. to 85° C.

The drying process may be run under a reduced pressure from 66.7 Pa to 50.7 kPa (0.5 to 380 mm Hg) (starting at atmospheric pressure). While not a required condition, reduced pressure assists in the speed of removal of water from the sulfated oligomer and water mixture, without the risk of reducing color purity of the dried sulfated oligomer and increasing the amount of an undesired side reaction.

If dimethyl sulfate is utilized in step a) above, any resulting methanol from the sulfated oligomer and water mixture will also be driving off in this stage. The amount of methanol remaining in the dried sulfated oligomer is from 0 wt % to 20 wt % by weight of the dried sulfated oligomer.

Step (c) Neutralization Step

The resulting sulfated oligomer of step (a) or optionally the dried sulfated oligomer mixture of step (b), as it is in acid form, is then neutralized by the addition of a neutralization agent. Suitable neutralization agents include hydroxide solution (50 wt %), other examples of suitable neutralization agents include sodium hydroxide and potassium hydroxide. The neutralization agent is added to the sulfated oligomer or dried sulfated oligomer in an amount from a Normality equivalent of acid present in the sulfated oligomer or dried sulfated oligomer to a 20% excess of the Normality equivalent of acid to insure the sulfated oligomer or dried sulfated oligomer is alkaline.

EXAMPLES

Sulfation of Anydrous Formula (II) to 30% Sulfation Of Available Sulfation Sites Heat a mixture of dry formula (II) (18.7 grams, 0.00377 moles), 30 mole % concentrated sulfuric acid (0.58 grams of 96.4 wt % sulfuric acid, 0.00566 moles), as determined by Formula (I), at 80° C. at 66.7 Pa (0.5 mm Hg) pressure. The following amounts of sulfation, sampled at the designated time period and as determined via $^1$H-NMR analysis (D$_2$O NaOD) result:

| Time | % sulfation of available sulfation sites |
|---|---|
| 15 minutes | 24% |
| 1 Hour | 26% |
| 2 Hours | 28% |

Sulfation of Aqueous Solution of Formula (II) to 30% Sulfation of Available Sulfation Sites Heat a mixture comprising a solution of 80 wt % active formula (II) and water, with the balance of the solution being water, (16.3 grams of 80 wt % formula (II), 0.00262 moles) and 30 mole % concentrated sulfuric acid (0.40 grams of 96.4 wt % sulfuric acid, 0.00393 moles), as determined by formula (I), at 60-65° C. at 101 kPa (1 atm) pressure. The following amounts of sulfation sampled at the designated time period and as determined via $^1$H-NMR analysis (D$_2$O NaOD) result:

| Time | % sulfation of available sulfation sites |
|---|---|
| 1 Hour | no sulfation |
| 2 Hour | no sulfation |

Decrease the pressure to 60-65° C. at 1.47 kPa (11 mm Hg) pressure:

| Time | % sulfation of available sulfation sites |
|---|---|
| 1 Hour | Trace |
| 2 Hour | Trace |
| 5 Hour | Trace |

Increase the temperature to 80° C. at 1.47 kPa (11 mm Hg) pressure:

| Time | % sulfation of available sulfation sites |
|---|---|
| 1 Hour | 8% |
| 2 Hour | 11% |
| 5 Hour | 14% |
| 8 Hour | 21% |

Sulfation of Aqueous Formula (II) to 30% Sulfation of Available Sulfation Site Using Two Fold Excess of Sulfuric Acid to Decrease Reaction Time Heat a mixture comprising a solution of 80 wt % active formula (II) and water, with the balance of solution being water (13.3 grams of 80 wt % formula (II), 0.00215 moles) and 60 mole % concentrated sulfuric acid (30 mole %*2 excess) (0.65 grams of 96.4 wt % sulfuric acid 0.00645 moles), as determined by formula (I), at 80° C. at 1.33 kPa (10 mm Hg) pressure. The following amounts of sulfation sampled at the designated time period and as determined via $^1$H-NMR analysis (D$_2$O NaOD) result:

| Time | % sulfation of available sulfation sites |
|---|---|
| 1 Hour | 5.4% Sulfation |
| 2 Hour | 10.6% |
| 3 Hour | 12.8% |
| 4 Hour | 18.3% |
| 5 Hour | 25.2% |

Sulfation of Aqueous Solution of Formula (II) to 30% Sulfation of Available Sulfation Sites Heat a mixture comprising a solution of 80 wt % active formula (II) and water, with the balance of the solution being water (14.0 grams of 80 wt % of formula (II), 0.00339 moles) and 30 mole % concentrated sulfuric acid (0.34 grams of 96.4 wt % sulfuric acid, 0.00339 moles), as determined by formula (I), at 80-85° C. at 1.33 kPa (10 mm Hg) pressure. The following amounts of sulfation sampled at the designated time period and as determined via $^1$H-NMR analysis (D$_2$O NaOD) result:

| Time | % sulfation of available sulfation sites |
| --- | --- |
| 1 Hour | 0.4% Sulfation |
| 2 Hour | 4.8% |
| 3 Hour | 8.8% |
| 4 Hour | 12.3% |
| 5 Hour | 16% |
| 6 Hour | 16% |

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for sulfating oligomers and polymers comprising the steps of:

a) sulfating an oligomer or polymer selected from polyamines having the formula (III):

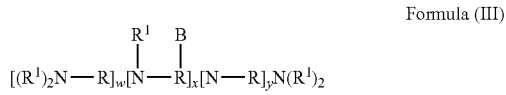

Formula (III)

wherein:
   each R unit is selected from moieties of the formula $-(R^3O)_w R^4-$ wherein:
   $R^3$ and $R^4$ are each independently selected from the group consisting of $C_2$-$C_8$ linear alkylene, $C_3$-$C_8$ branched alkylene, phenylene, substituted phenylene, or mixtures thereof;
   the index w is from 0 to 10;
   each $R^1$ unit is selected from moieties of the formula;

$-(R^2O)_t Y$ wherein:
   $R^2$ is ethylene, 1,2-propylene, or mixtures thereof;
   Y is hydrogen, and
   the value of the index t is from 1 to 100;
   the values of the indices w', x', and y' are selected such that the polyamine has a backbone weight average molecular weight prior to modification of from 600 daltons to about 3000 daltons, and any mixture thereof; by the addition of sulfuric acid to make a sulfated oligomer and water mixture;

b) optionally driving off the water from the sulfated oligomer or polymer and water mixture to make a dried sulfated oligomer or polymer mixture;

c) neutralizing the sulfated oligomer or polymer mixture of step (a) or optionally the dried sulfated oligomer or polymer mixture of step (b) by mixing with neutralization agent.

2. The process of claim 1 wherein the sulfation of step a) may further sulfate the oligomer or polymer by adding sulfuric acid, dimethyl sulfate, water and a non-sulfating acid, to make a oligomer or polymer mixture, such that the oligomer or polymer mixture has a pH of 2.

3. The process of claim 1 wherein the process comprises the driving step of b) and further comprises driving off the water by heating the sulfated oligomer or polymer and water mixture at a temperature from 20 to 150° C.

4. The process of claim 3 wherein the driving step of b) further comprises driving off the water by heating the sulfated oligomer or polymer and water mixture at a temperature from 20° C. to 85° C. such that the oligomer/polymer is liquid.

5. The process of claim 4 wherein the driving step of b) is at a temperature of 80° C.

6. The process of claim 1 wherein the driving step of b) comprises adding an inert solvent that azeotropes with water.

7. The process of claim 6 wherein the inert solvent is selected from benzene.

8. The process of claim 3 wherein the driving step of b) further comprises driving off the water by having a pressure from about 66.7 Pa to about 50.7 kPa.

9. The process of claim 1 wherein the driving step of b) is such that the dried oligomer or polymer mixture comprises from 0.01 wt % to about 20 wt % by weight of the dried oligomer or polymer mixture of water.

10. The process of claim 2 wherein the driving step of b) is such that the dried oligomer or polymer mixture comprises from 0.01 wt % to about 20 wt % by weight of the dried oligomer or polymer mixture of water.

11. The process of claim 10 wherein the driving step of b) is such that the dried oligomer or polymer mixture comprises from 0 wt % to 20% by weight of the dried oligomer or polymer mixture of methanol.

12. A process for sulfating oligomers and polymers according to claim 1 wherein the polyamine is selected from polyamines having the formula (V):

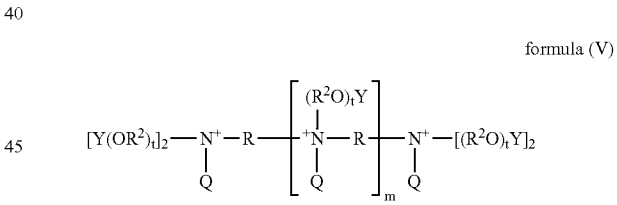

formula (V)

wherein:
R of formula (V) have the formula $-(R^3O)_w R^4-$ wherein $R^3$ and $R^4$ are each independently selected from the group consisting of $C_2$-$C_8$ linear alkylene, $C_3$-$C_8$ branched alkylene, phenylene, substituted phenylene, and mixtures thereof;
$R^2$ of formula (V) is ethylene, 1,2-propylene, and mixtures thereof;
Y of formula (V) is hydrogen,
O of formula (V) is methyl or benzyl;
the value of the index t of formula (V) is from 1 to 100,
the index m is from 0 to 20; and
the index w is from 1 to 10.

* * * * *